US008313946B2

(12) United States Patent
Becwar et al.

(10) Patent No.: US 8,313,946 B2
(45) Date of Patent: Nov. 20, 2012

(54) LIQUID-BASED METHOD FOR PRODUCING PLANT EMBRYOS

(75) Inventors: Mike Becwar, Summerville, SC (US); John Clark, Summerville, SC (US); LeShaun Swinton, Summerville, SC (US); Narender Nehra, Summerville, SC (US); Tim Stout, Summerville, SC (US)

(73) Assignee: Arborgen Inc., Ridgeville, SC (US)

( * ) Notice: Subject to any disclaimer, the term of this patent is extended or adjusted under 35 U.S.C. 154(b) by 406 days.

(21) Appl. No.: 12/440,280

(22) PCT Filed: Sep. 5, 2007

(86) PCT No.: PCT/US2007/019294
§ 371 (c)(1),
(2), (4) Date: Aug. 11, 2010

(87) PCT Pub. No.: WO2008/030423
PCT Pub. Date: Mar. 13, 2008

(65) Prior Publication Data
US 2010/0297770 A1    Nov. 25, 2010

Related U.S. Application Data

(60) Provisional application No. 60/842,985, filed on Sep. 8, 2006.

(51) Int. Cl.
*C12N 5/00* (2006.01)
*C12N 5/02* (2006.01)
(52) U.S. Cl. ........................ 435/422; 435/420
(58) Field of Classification Search .................. 435/422, 435/420, 430.1, 410
See application file for complete search history.

(56) References Cited

U.S. PATENT DOCUMENTS

| | | | |
|---|---|---|---|
| 6,627,441 B1 * | 9/2003 | Attree | 435/422 |
| 7,452,722 B2 * | 11/2008 | Gupta et al. | 435/422 |
| 7,520,089 B2 * | 4/2009 | Hartle et al. | 47/58.1 SE |
| 2005/0188436 A1 | 8/2005 | Gupta et al. | |
| 2005/0198713 A1 | 9/2005 | Gupta et al. | |

OTHER PUBLICATIONS

The International Search and Written Opinion for the corresponding International Patent Application No. PCT/US2007/019294. (15 pgs.), Mar. 6, 2009.
Database Biosis [Online] *Biosciences Information Service*, 1999, Yang Ying-Gen et al: "Studies on the factors Affecting of Somatic Embryogenesis in Embryonic Cell Suspension Culture of *Picea wilsonii*", vol. 21, No. 1, pp. 114-120. (XP002474296).
Gorbatenko, et al., "Desiccation-tolerant Somatic Embryos of Norway Spruce (*Picea abies*) can be Produced in Liquid Cultures and Regenerated into Plantlets", *International Journal of Plant Sciences*, vol. 162, No. 6, 2001, pp. 1211-1218.
Kobayashi, et al., "4-Hydroxybenzyl Alcohol Accumulates in Suspension-Cell Cultures and Inhibits Somatic Embryogenesis in Carrot", *Physiologia plantarum*, vol. 112, No. 2, 2001, pp. 280-284.
Pullman, et al., "Improving Loblolly Pine Somatic Embryo Maturation: Comparison of Somatic and Zygotic Embryo Morphology, Germination, and Gene Expression", *Plant Cell Reports*, vol. 21, No. 8, 2003, pp. 747-758.

(Continued)

*Primary Examiner* — Kent L Bell
(74) *Attorney, Agent, or Firm* — Foley & Lardner LLP

(57) ABSTRACT

The present invention relates to methods for developing embryos and producing germination-competent embryos using a liquid embryo development media.

29 Claims, 2 Drawing Sheets

OTHER PUBLICATIONS

Salaj, et al., "Embryogenic Suspension Cultures of *Pinus nigra* Am.: Growth Parameters and Maturation Ability", *ACTA Physiologiae plantarum*, vol. 29, No. 3, 2007, pp. 225-231.

Tang, et al., "Plant Regeneration from Embryogenic Cultures Initiated from Mature Loblolly Pine Zygotic Embryos", In Vitro *Cellular & Development Biology*, vol. 37, No. 5, 2001, pp. 558-563.

\* cited by examiner

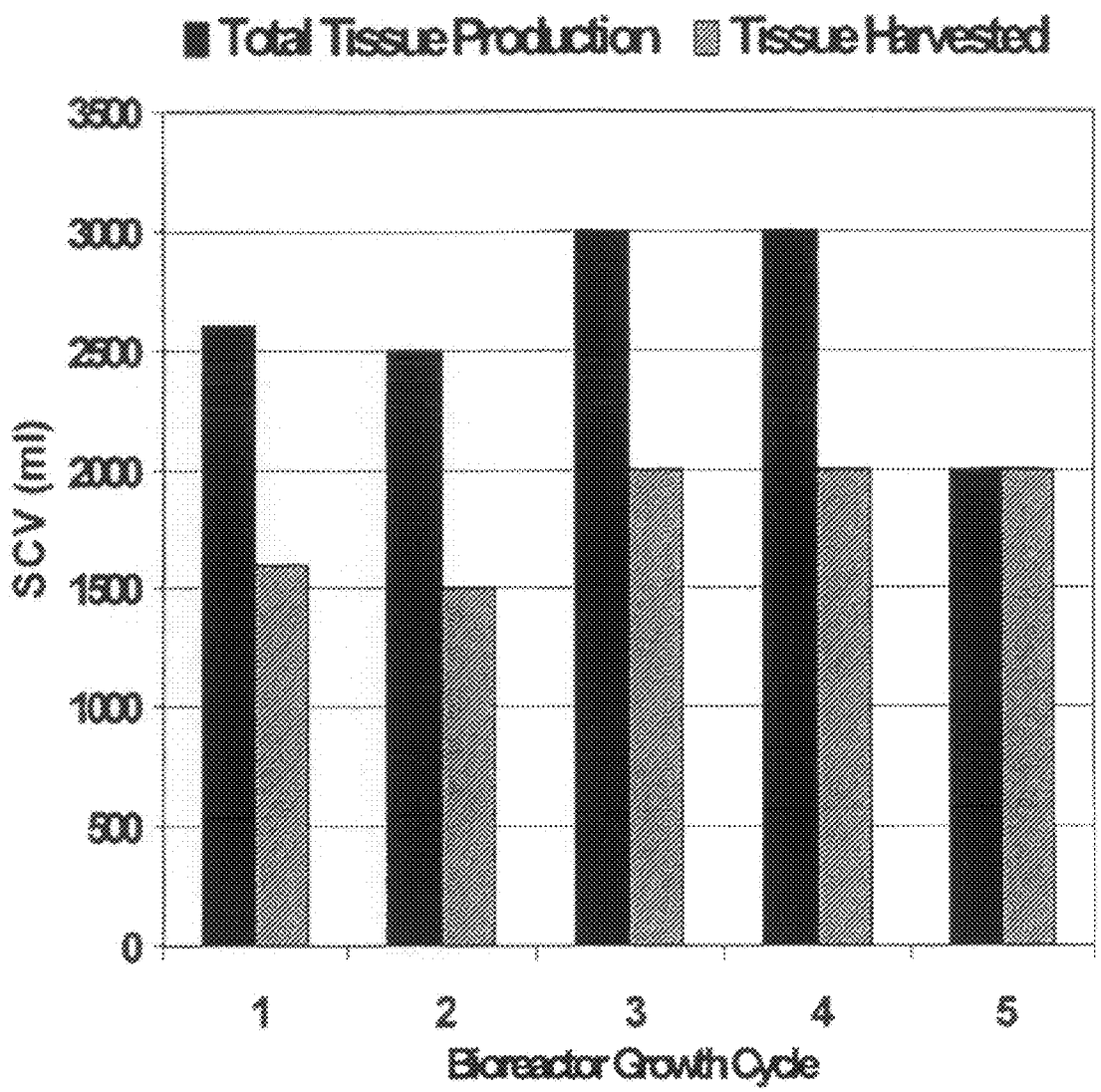

LIQUID-BASED METHOD FOR PRODUCING PLANT EMBRYOS

FIELD OF THE INVENTION

The present invention relates to methods for developing embryos and producing germination-competent embryos using liquid embryo development media.

BACKGROUND OF THE INVENTION

Many trees and woody horticultural species, such as loblolly pine, Radiata pine, and eucalyptus, have lengthy breeding cycles. For this reason, using traditional breeding programs to incorporate new and commercially desirable traits into those trees and woody species is time-consuming and cumbersome. It takes too long, or it is not feasible, for instance, to back-cross trees in order to introduce a new genetic trait into a desired line. Furthermore, it is often difficult to ramp up production of those trees and species to levels that are suitable for large-scale propagation, by simply employing conventional vegetative or clonal propagation methods, including those frequently used for somatic embryogenesis.

This is largely because conventional vegetative and clonal propagation strategies, particularly somatic embryogenesis strategies, require numerous manual handling steps that involve physical transfer of embryos from one gelled surface to another. The starting explants, e.g., seeds, are typically placed onto a Petri dish with medium that contains plant growth regulators and nutrients for 6-8 weeks, until embryogenic tissue forms. The tissue is then bulked up on either a gelled or liquid maintenance medium to obtain sufficient mass for subsequent use. The resultant embryogenic tissue is then transferred to another Petri dish that contains a maturation medium to promote formation of somatic embryos. Embryos are then conditioned until they are ready for germination. When the germinated embryos have grown large enough, they are then transferred to a greenhouse and eventually planted in the field.

This conventional gel-based Petri dish methodology is cumbersome and time-consuming and does not lend itself to routine automation or commercial scale-up. Hence, under the traditional system, large-scale production typically relies on manual labor, which can prove to be expensive. Approximately sixty-percent of costs involved in large-scale propagation, for instance, are attributable to man-power involved in "rooting" efforts. See Mass propagation of conifer trees in liquid cultures—progress towards commercialization. In: Hvoslef-Eide A. K. and W. Preil (eds.) Liquid culture systems for in vitro plant propagation. Springer. Netherlands, pages 389-402, 2005.

Gel-based culturing systems are not readily amenable to automation since they require manual intervention. By contrast, liquid culturing systems for somatic embryogenesis can be automated, which makes it easier and more efficient to handle and change liquid media. Indeed, tissue and cell transfer, sub-culturing, and harvesting can all be accomplished efficiently in a liquid culture systems. See Hvoslef-Eide A. K. and W. Preil (eds.) Liquid culture systems for in vitro plant propagation. Springer. Dordrecht, The Netherlands, 2005.

Large-scale "bioreactor" vessels, which propagate cell and tissue cultures in large volumes of liquid, therefore, are useful for maintaining and bulking-up embryogenic cells and tissues (Hvoslef-Edie and Preil 2005, supra). The problem is that these large-scale bioreactors and non-gel culturing systems have not proven adaptable for producing conifer somatic embryos.

Other systems have therefore evolved that employ an intermediate step of culturing conifer tissues on membrane rafts that are floated on liquid medium. Such systems, often referred to as "temporary immersion" systems, however, prove costly and complex when they are adapted to perform at a large scale levels for conifer somatic embryogenesis. See Vagner et al., in Hvoslef-Eide A. K. and W. Preil (supra) at pages 295-302.

Another issue concerning large-scale production of conifer somatic embryos is the use, conventionally, of polyethylene glycol in development media. It is well accepted that a relatively high concentration of polyethylene glycol in gel-based development medium is a routine and standard method for stimulating embryo development and increasing embryogenic cultures in conifers. For instance, Gupta used highly concentrated amounts of polyethylene glycol (PEG), such as 10% to 18%, in both gelled, i.e., "solid," and liquid embryo development media for development of Douglas fir somatic embryos. See U.S. Patent Application Nos. 2005/0003415, 2005/0026281, 2005/0188436, and 2005/0198713, and U.S. Pat. No. 5,036,007. In those systems, absorbent pads were soaked with liquid development medium and embryogenic tissue placed on the pads.

Similarly, Attree et al., Ann. Bot. 68:519-525. 1991, observed a 3-fold increase in the maturation frequency of white spruce somatic embryos on gel-based development media containing an optimum of 5% to 7.5% polyethylene glycol. Attree found that embryo development and production was not as effective when lower concentrations of polyethylene glycol were used in the gel media.

Attree later reported on a technique for transferring embryogenic suspension cultures of *Picea glauca* onto an absorbent pad, which was in contact with liquid embryo development medium, but with the surface of the pad above the liquid medium surface. See Attree et al., Plant Cell Reports. 13:601-606. 1994. Hence, the embryos were exposed to the atmosphere inside the chamber, rather than directly in the liquid. Under Attree's system, 6,314 cotyledon stage somatic embryos were harvested from one chamber using 3 liters of medium in 7 weeks (from 10 grams of embryogenic starting tissue grown from a liquid culture). This equates to just about 2 somatic embryos per ml of liquid embryo development medium used in the chamber.

In U.S. Pat. No. 6,340,594, Attree developed a continuous-flow solid-support bioreactor. In this system, the embryogenic tissue and resulting embryos were not submerged in the liquid medium. Hence, embryo development did not occur completely in liquid medium.

Likewise, Paques also reported that only those conifer *Picea abies* embryos that were directly in contact with the atmosphere, as opposed to those submerged in liquid, were able to reach the cotyledonary stage. See Paques et al., Acta. Hort. 319:95-100, 1992. They found that maturation of the conifer embryos could not be achieved when the embryos were placed directly in a liquid medium. Specifically, embryos in contact with the liquid medium failed to develop. Vagner et al. in Hvoslef-Eide A. K. and W. Preil (eds.) Liquid culture systems for in vitro plant propagation. Springer. Netherlands, pages 389-402, 2005, reported that cultivation of Norway spruce embryogenic cell lines in liquid embryo development medium resulted in severe decrease in the number of developed embryos compared to development on gelled or an intermediate raft system.

Ingram and Mavituna, Plant Cell Tiss. Org. Cult. 61:87-96. 2000, found that bioreactor type can influence proliferative growth of *Picea* embryogenic cultures, although they did not examine embryo development directly in liquid culture bioreactor vessels. Instead, they used a submerged culture system whereby proliferating cells from the bioreactor were transferred to a layer of liquid embryo development medium overlaying gelled embryo development medium. They found that cotyledonary embryo production was very much reduced, by an average of 88%, in this combined liquid and gelled culture system compared to the gelled culture in one cell line and slightly reduced (by 27%) in another cell line. This liquid-gel combination system does not provide a viable system for large-scale embryo production.

Accordingly, it is established that embryo development in *Picea* species is generally better if proliferating cell cultures are transferred to gelled embryo development medium, regardless of whether they undergo the proliferation phase in a standard flask system or in a bioreactor system. Neither Pacques (1992) nor Ingram and Mavituna (2000) employ a completely liquid embryo development system.

While it is well established that polyethylene glycol be included in embryo development media, it also is well established that polyethylene glycol can harm embryos. Hence, Hogberg et al., Scand. J. For. Res. 16:295-304; 2001, describe the detrimental effects on germination of conifer somatic embryos matured on gelled, i.e., non-liquid-based, embryo development medium containing PEG. PEG also may be omitted from gelled embryo development medium during the latter phase of embryo development. See also U.S. Patent Nos. 5,731,204 and 5,731,191, which are incorporated herein by reference.

The gelled method, while reducing the detrimental effects of PEG, however, does not lend itself to large-scale production. This is because (1) both the embryo development and the post embryo development phases require a gelled medium, and (2) removal of PEG during embryo development requires manually transferring the tissue to a new gelled medium. Aside from these practical downsides, scaling up of such methods can prove costly and burdensome.

There has been, however, complete development of Norway spruce somatic embryos in liquid medium. See Gorbatenko et al. Int. J. Plant Sci. 162 (6):1211-1218, 2001. Gorbatenko, however, used continuous and prolonged exposure to PEG at high concentrations, e.g., 7.5%, which may have deleterious affects on embryo regeneration efficiency.

A bioreactor system for maturation of conifer somatic embryos that utilizes a tissue immobilization phase following a submerged tissue phase is described in U.S. Patent Application 2005/0287660, which is incorporated herein by reference. This two phase system is complex and requires more manipulation and regulation of the tissue compared to a completely liquid embryo development system as described by our invention. Thus, this bioreactor system does not achieve the advantages afforded by a completely liquid embryo development system as obtained in our invention.

Typically, therefore, conventional embryo development methods (i) use gelled media and are therefore not readily amenable to large-scale production requirements, (ii) use a partial liquid/gel method where embryos are placed onto a surface that is saturated with liquid media, (iii) use liquid-based bioreactors where the liquid media passes under embryos that are in contact with, but elevated above, the passage of liquid, (iv) use polyethylene glycol at concentrations that are known to have detrimental effects on embryo development. Hence, conventional methods for developing embryos can be encumbered by one or more of these parameters or limitations.

The present inventive "all-liquid" method avoids these drawbacks. In this method, embryos develop entirely within the desired volume of liquid without direct exposure to the atmosphere. Further, where polyethylene glycol is incorporated into the liquid medium it is (a) at levels below which are normally used, (b) only temporarily present in the liquid medium, or (c) gradually increased or decreased in concentration at the will of the operator. An added benefit of the presently inventive method is that it increases the numbers of germination-competent embryos that can be produced per volume of liquid media and thereby accelerates the plant production potential and concomitantly decreases handling costs and manual labor costs, as well as the embryo production costs.

SUMMARY OF THE INVENTION

In one aspect of the present invention is a method for developing plant embryos from proliferative plant cells, comprising incubating proliferative plant cells for a period of time in a Liquid Embryo Development Medium that comprises (i) phytohormone, (ii) a source of reduced nitrogen, and (iii) carbohydrate, wherein embryos are developed after the period of time. In one embodiment, the method of claim 1, wherein the embryonic development medium does not comprise a non-permeating osmotic agent.

In another embodiment, the embryonic development medium does not comprise polyethylene glycol.

In one embodiment, the phytohormone is abscisic acid (ABA). In another embodiment, the concentration of ABA is from about 1 mg/l to about 100 mg/l. In another embodiment, the concentration of ABA is about 21 g/l.

In one embodiment, the source of reduced nitrogen is an amino acid. In another embodiment, the amino acid is L-glutamine. In a further embodiment, the concentration of glutamine is from about 0.1 g/l to about 6.0 g/l. In a preferred embodiment, the concentration of L-glutamine is about 1.45 g/l.

In one embodiment, the carbohydrate is a saccharide, such as, but not limited to mono- and di-saccharide sugars. Such sugars include but are not limited to maltose, sucrose, and fructose.

In one embodiment, the liquid embryonic development medium comprises from about 1% to about 10% maltose. In another embodiment, the liquid embryonic development medium comprises about 2% maltose. In another embodiment, the liquid embryonic development medium further comprises activated carbon. In one embodiment, the concentration of activated carbon is from about 0.1 g/l to about 2.5 g/l. In a preferred embodiment, the concentration of activated carbon is about 1.25 g/l.

In another embodiment, the liquid embryonic development medium further comprises myo-inositol. In another embodiment, the concentration of myo-inositol is from about 10 mg/l to about 1000 mg/l. In a further embodiment, the concentration of myo-inositol is about 100 mg/l.

In one particular embodiment, the liquid embryonic development medium does not contain a gelling agent.

In another embodiment, the osmolarity of the liquid embryonic development medium is from about 50 mmol/kg to about 200 mmol/kg. In a preferred embodiment, the osmolarity of the liquid embryo development medium is about 82 mmol/kg. In on embodiment; the osmolarity of the liquid embryo development medium is about 40 mmol/kg, about 50 mmol/kg, about 60 mmol/kg, about 70 mmol/kg, about 80 mmol/kg, about 90 mmol/kg, about 100 mmol/kg, about 110 mmol/kg, about 120 mmol/kg, about 130 mmol/kg, about 140 mmol/kg, about 150 mmol/kg, about 160 mmol/kg, about 170 mmol/kg, about 180 mmol/kg, about 190 mmol/kg, about 200 mmol/kg, about 210 mmol/kg, about 220 mmol/kg, about 230 mmol/kg, about 240 mmol/kg, about 250 mmol/kg, or more.

In one embodiment, the proliferative plant cells are incubated in the liquid embryo development medium for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, or more than about 24 weeks. In another embodiment, the proliferative plant cells are incubated in the liquid embryo development medium for no more than 1 to 7 weeks. In another embodiment, the proliferative plant cells are incubated in the liquid embryo development medium for no more than 3 to 5 weeks. In another embodiment, the proliferative plant cells are incubated in the liquid embryo development medium for no more than 5 weeks.

In one embodiment, the proliferative plant cells are incubated in the liquid embryo development medium until they reach a optimal settled cell volume (SCV). In one embodiment, the proliferative plant cells are conifer cells.

In one embodiment, the conifer is selected from the group consisting of Eastern white pine, Western white, Sugar pine, Red pine, Pitch pine, Jack pine, Longleaf pine, Shortleaf pine, Loblolly pine, Slash pine, Virginia pine, Ponderosa pine, Jeffrey pine, Pond pine, and Lodgepole pine, Radiata pine and hybrid crosses thereof.

In another embodiment, the proliferative cells are incubated in about 10 ml to about 100 liters of the liquid embryonic development medium.

According to one embodiment, the method further comprises conditioning the retrieved somatic embryos for a period of time, wherein the somatic embryos become germination-competent after the conditioning period.

In one embodiment, the Liquid Embryo Development Medium does not comprise polyethylene glycol.

In another embodiment, the conditioning step entails storing the retrieved somatic embryos in a high relative humidity environment for the period of time. In one embodiment, the somatic embryos are stored in a high relative humidity environment for 1-7 weeks. In another embodiment, the proliferative plant cells are incubated in the liquid embryonic development medium for no more than 5 weeks.

In one embodiment, germination-competent somatic embryos are produced no more than 8 weeks after the proliferative plant cells are incubated in the liquid embryonic development medium.

The present invention also provides a method for determining an optimal settled cell volume for developing plant embryos comprising (1) adding a volume of proliferative plant cells to a volume of liquid embryonic development medium to produce a solution of cells in a vessel, (2) agitating the solution for a first period of time, (3) measuring cell density at least once during and/or after the first period of time, (4) further agitating the solution for a second period of time, (5) recording the number of embryos that have developed in the solution after the second period of time, (6) repeating steps (1) to (5) by adding a different volume of proliferative plant cells to the same volume of liquid embryonic development medium in another vessel and shaking and further shaking the solution for same periods of time, and (7) comparing the recorded numbers of plant embryos that have developed in the solutions, wherein the cell density value for the volume of proliferative plant cells that produces the most number of embryos is an optimal cell density for developing embryos from that species of plant cells.

In one embodiment, the first period of time is about 1-3 weeks. In another embodiment, the second period of time is about 2 weeks.

Another aspect of the present invention is a method for determining an optimal settled cell volume for developing plant embryos comprising (1) adding a volume of proliferative plant cells to a volume of liquid embryonic development medium to produce a solution of cells, (2) agitating the solution for a first period of time, (3) removing an aliquot of the solution after the first period of time to a vessel, (4) allowing the cells in the aliquot of the solution to settle as a layer of cells, (5) measuring and recording the height of the cell layer to generate a settled cell volume (SCV) value, (6) further agitating the solution for a second period of time, (7) recording the number of embryos that have developed in the solution after the second period of time, (8) repeating steps (1) to (7) by adding a different volume of proliferative plant cells to the same volume of liquid embryonic development medium and shaking and further shaking the solution for same periods of time, and (9) comparing the recorded numbers of plant embryos that have developed in the solutions, wherein the SCV value for the volume of proliferative plant cells that produces the most number of embryos is an optimal SCV for developing embryos from that species of plant cells.

Another aspect of the present invention is a one-vessel method for developing plant embryos at commercial levels, comprising (1) incubating a volume of proliferative plant cells in a volume of liquid proliferation medium in a vessel for a first period of time to enhance cell proliferation, (2) exchanging the volume of liquid initiation medium after the first period of time with a volume of liquid embryonic development medium, and (3) incubating the proliferative plant cells in the liquid embryonic development medium for a second period of time in the same vessel, wherein plant embryos are developed after the second period of time, and wherein the liquid embryonic development medium comprises (i) phytohormone, (ii) a source of reduced nitrogen, and (iii) metabolizable carbohydrate, such as sugars like maltose, glucose, and sucrose.

In one embodiment, the liquid embryonic development medium does not comprise a non-permeating osmotic agent. In one embodiment, the liquid embryonic development medium does not comprise polyethylene glycol.

In another embodiment, the volume of liquid initiation medium in the vessel is about 1-50 liters, 1-60 liters, 1-70 liters, 1-80 liters, 1-90 liters, 1-100 liters or more than 100 liters.

In one embodiment, the step of exchanging the liquid initiation medium for the embryonic development medium is automated.

In another embodiment, the vessel is a bioreactor.

In one embodiment, the bioreactor is a vessel, which comprises (1) a 2-20 liter-capacity bottle that comprises (i) a first port to supply air to the bottle, (ii) a second port to allow air to escape from the bottle, (iii) a third port for dispensing fresh medium or new medium from a reservoir into the bottle. In one embodiment, the step of exchanging the liquid initiation medium for the embryonic development medium in the bioreactor is performed under vacuum, whereby the liquid initiation medium is removed from the bottle and liquid embryonic development medium is drawn into the bottle from the reservoir via the third port.

In one embodiment, the method further comprises conditioning the developed embryos in the vessel for a period of time, wherein the embryos become germination-competent after the conditioning period. In one embodiment, the conditioning step entails removing the liquid embryonic development medium in the vessel and converting the atmosphere inside the vessel into a high relative humidity environment for the period of time.

In another embodiment, the developed embryos are stored in the high relative humidity environment for 1-5 weeks. In one embodiment, the proliferative plant cells are incubated in the liquid embryonic development medium in the vessel for no more than 5 weeks. In another embodiment, the method further comprises retrieving embryos that have developed in the liquid embryo development medium after the period of time. In one embodiment, the Liquid Embryo Development Medium comprises inorganic compounds. In one embodiment, the Liquid Embryo Development Medium comprises the inorganic compounds denoted in Table 2. According to the described method, In one embodiment, the optimal settled cell volume (SCV) has been predetermined.

Another aspect of the present invention is a method for developing plant embryos from proliferative plant cells, consisting of incubating proliferative plant cells for a period of time in a Liquid Embryo Development Medium that comprises (i) one or more phytohormones, (ii) a source of reduced nitrogen, and (iii) carbohydrate, wherein the Liquid Embryo Development Medium does not contain polyethylene glycol, and wherein embryos are developed after the period of time.

In another embodiment, the coniferous tree is selected from the group consisting of Eastern white pine, Western white, Sugar pine, Red pine, Pitch pine, Jack pine, Longleaf pine, Shortleaf pine, Loblolly pine, Slash pine, Virginia pine, Ponderosa pine, Jeffrey pine, Pond pine, and Lodgepole pine, Radiata pine and hybrid crosses thereof. In another preferred embodiment, the coniferous tree is selected from the group consisting of, but not limited to, species of the genera *Abies, Araucaria, Cedrus, Chamaecyparis, Cryptomeria, Cryptomeria, Larix, Metasequoia, Picea, Pinus, Pseudotsuga, Sequoia, Sequoiadendron, Taxodium, Taxus, Thuja, Tsuga,* and hybrid crosses of species thereof.

Specific examples of each of such coniferous trees includes: *Abies alba,* European silver fir; *Abies amabilis,* Pacific silver fir; *Abies balsamea,* Balsam fir; *Abies bornmuelleriana,* Turkish fir; *Abies concolor,* White fir; *Abies fraseri,* Fraser fir; *Abies grandis,* Grand fir; *Abies koreana,* Korean fir; *Abies lasiocarpa,* Alpine fir; *Abies nordmanniana,* Nordman fir; *Abies procera,* Noble fir; *Araucaria angustifolia,* Parana pine; *Araucaria araucana,* Monkeypuzzle tree; *Araucaria bidwillii,* Bunya pine; *Araucaria cunninghamii,* Hoop pine; *Cedrus atlantica,* Atlas cedar; *Cedrus deodara,* Deodar cedar; *Chamaecyparis lawsoniana,* Port-Orford-cedar; *Chamaecyparis pisifera,* Sawara cypress; *Cryptomeria japonica,* Japanese cedar (Japanese cryptomeria); *Cuppressocyparii leylandii,* Leyland Cypress; *Larix decidua,* European larch; *Larix occidentalis,* Western larch; *Metasequoia glyptostroboides,* Dawn redwood; *Picea abies,* Norway spruce; *Picea engelmannii,* Englemann spruce; *Picea glauca,* White spruce; *Picea mariana,* Black spruce; *Picea pungens,* Colorado blue spruce; *Picea rubens,* Red spruce; *Picea sitchensis,* Sitka spruce; *Pinus banksiana,* Jack pine; *Pinus caribaea,* Caribbean pine; *Pinus contorta,* lodgepole pine; *Pinus echinata,* Shortleaf pine; *Pinus edulis,* Pinyon pine; *Pinus elliotii,* Slash pine; *Pinus jeffreyi,* Jeffrey Pine; *Pinus korariensis,* Korean pine; *Pinus lambertiana,* Sugar pine; *Pinus merkusii,* Sumatran pine; *Pinus monticola,* Western white pine; *Pinus nigra,* Austrian pine; *Pinus palustris,* Longleaf pine; *Pinus pinaster,* Maritime pine; *Pinus ponderosa,* Ponderosa pine; *Pinus rigida,* Pitch pine; *Pinus radiata,* Radiata pine; *Pinus resinosa,* Red pine; *Pinus serotina,* Pond pine; *Pinus strobus,* Eastern white pine; *Pinus sylvestris,* Scots (Scotch) pine; *Pinus taeda,* Loblolly pine; *Pinus virginiana,* Virginia pine; *Pseudotsuga menziesii,* Douglas-fir; *Sequoia sempervirens,* Redwood; *Sequoiadendron giganteum,* Sierra redwood; *Taxodium ascends,* Pond cypress; *Taxodium distichum,* Bald cypress; *Taxus baccata,* European yew; *Taxus brevifolia,* Pacific or Western yew; *Taxus cuspidaia,* Japanese yew; *Thuja occidentalis,* Northern white-cedar; *Thuja plicata,* Western red cedar; *Tsuga canadensis,* Eastern hemlock; *Tsuga heterophylla,* Western hemlock.

In another embodiment, the coniferous plant tissue is a Southern Yellow pine. In yet another embodiment, the Southern Yellow pine is selected from the group consisting of *Pinus taeda, Pinus serotina, Pinus palustris,* and *Pinus elliottii.*

In another embodiment, therefore, the plant tissue, such as embryogenic tissue or a somatic embryo is from a tree selected from the group consisting of chestnut, ash, beech, basswood, birch, black cherry, black walnut/butternut, chinkapin, cottonwood, elm, eucalyptus, hackberry, hickory, holly, locust, magnolia, maple, oak, poplar, red alder, royal paulownia, sassafras, sweetgum, sycamore, tupelo, willow, and yellow-poplar, and intra- and inter-species hybrid crosses thereof. Particularly preferred trees in this group are eucalyptus, sweetgum, and American Chestnut.

In another embodiment, the percentage of a non-permeating osmotic agent, such as polyethylene glycol, in the inventive Liquid Embryo Development Medium is 1%, 2%, 3%, 4%, 5%, 6%, 7%, 8%, 9%, 10%, 11%, 12%, 13%, 14%, 15%, 16%, 17%, 18%, 19%, or 20%. In one embodiment, the percentage of a non-permeating osmotic agent, such as polyethylene glycol, in the inventive Liquid Embryo Development Medium is less than 7.5%, less than 7%, less than 6%, less than 5%, less than 4%, less than 3%, less than 2%, less than 1%. Any of the percentages of non-permeating osmotic agents may be used in the inventive Liquid Embryo Development Medium for a temporary period of time. For example, one may include 7% of PEG for 12 hours before removing PEG entirely or before reducing or increasing the percentage of PEG to another value. Hence, the present invention permits one to modulate the concentration of a non-permeating osmotic agent over the course of time of embryo development, by varying the percentage of PEG that is introduced into, or removed from, the inventive Liquid Embryo Development Medium.

In yet another embodiment, the inventive Liquid Embryo Development Medium contains a non-permeating osmotic agent, such as polyethylene glycol, only for a limited period of time. That is, one advantage of using a liquid medium is that the medium can readily be replaced at a desired time without manual manipulating the submerged plant tissue. Hence, in one embodiment, a plant tissue containing proliferative plant cells may be cultured in a Liquid Embryo Development Medium that does contain a certain percentage of non-permeating osmotic agent, such as polyethylene glycol, for a desired period of time. After that period of time, all of part of the medium containing the non-permeating osmotic agent may be drained or suctioned away from the vessel containing the plant tissue and simultaneously replaced with Liquid Embryo Development Medium that does not contain the non-permeating osmotic agent. Of course, this removal-replacement step may be conducted any number of times during the embryo development stage. Hence, the initial concentration of the non-permeating osmotic agent may become zero after the liquid replacement step, or the concentration of the non-permeating osmotic agent may be diluted down to a lower concentration. Accordingly, the present invention also contemplates the successive dilution of a non-permeating osmotic agent from a desired initial concentration to lower concentrations by liquid replacement, until the concentration of the agent is negligible or the liquid medium completely lacks the agent. This modulation can be performed over the course a day to several weeks.

Thus, in one embodiment, 1%, 2%, 3%, 4%, 5%, 6%, 7%, 8%, 9%, 10%, 11%, 12%, 13%, 14%, 15%, 16%, 17%, 18%, 19%, or 20% of a non-permeating osmotic agent may be included in the liquid embryo development medium for 1 minute, 2 minutes, 5 minutes, 10 minutes, 15 minutes, 20 minutes, 30 minutes, 45 minutes, 60 minutes, 2 hours, 3 hours, 4 hours, 5 hours, 6 hours 7 hours, 8 hours, 9 hours, 10 hours, 12 hours, 1 day, 2 days, 3 days, 4 days, 5 days or more or any period of time therein between before a volume of the medium is replaced completely or partially with a volume of Liquid Embryo Development Media that does not contain the non-permeating osmotic agent.

Non-permeating osmoticants, such as PEG, as well as permeating osmoticants, such as maltose and sucrose, may initiate a second messenger, perhaps ethylene, which has a developmental effect. The resulting osmotic stress may induce tissue in the system to increase production of ethylene, which then has a development promoting effect on the same or other tissue. Ethylene may affect the transition from a juvenile stage to some a more mature stage that is competent to complete development. Thus, modulating tissue exposure to ethylene may be a useful method for promoting or controlling the development process.

The percentage of treated embryos that germinate may be 1%, 2%, 3%, 4%, 5%, 6%, 7%, 8%, 9%, 10%, 11%, 12%, 13%, 14%, 15%, 16%, 17%, 18%, 19%, or 20%, 30%, 40%, 50%, 60%, 70%, 80%, 90%, or 100%, or any percentage integer in between. Thus, some or all of the embryos that are developed according to the present invention may germinate.

One mode of the present invention results in embryo production directly in a completely liquid medium that does not contain water soluble non-permeating osmotic agents. Therefore, this mode of the invention eliminates the undesirable or detrimental affects of PEG noted above and does so in a liquid system that can be readily scaled up for large commercial production.

The osmolarity of the liquid embryo development medium may be about 10 mmol/kg, 20 mmol/kg, 30 mmol/kg, 40 mmol/kg, 50 mmol/kg, 60 mmol/kg, 70 mmol/kg, 80 mmol/kg, 90 mmol/kg, 100 mmol/kg, 110 mmol/kg, 120 mmol/kg, 130 mmol/kg, 140 mmol/kg, 150 mmol/kg, 160 mmol/kg, 170 mmol/kg, 180 mmol/kg, 190 mmol/kg, or 200 mmol/kg, or any integer there in between. In one embodiment, the osmolarity of the liquid embryo development medium is about 70 mmol/kg, 71 mmol/kg, 72 mmol/kg, 73 mmol/kg, 74 mmol/kg, 75 mmol/kg, 76 mmol/kg, 77 mmol/kg, 78 mmol/kg, 79 mmol/kg, 80 mmol/kg, 81 mmol/kg, 82 mmol/kg, 83 mmol/kg, 84 mmol/kg, 85 mmol/kg, 86 mmol/kg, 87 mmol/kg, 88 mmol/kg, 89 mmol/kg, 90 mmol/kg, 95 mmol/kg, 100 mmol/kg, 105 mmol/kg, 110 mmol/kg, 115 mmol/kg, 120 mmol/kg, 125 mmol/kg, 130 mmol/kg, 135 mmol/kg, 140 mmol/kg, 145 mmol/kg, 150 mmol/kg, 155 mmol/kg, 160 mmol/kg, 165 mmol/kg, 170 mmol/kg, 175 mmol/kg, 180 mmol/kg, 185 mmol/kg, 190 mmol/kg, 195 mmol/kg, or 200 mmol/kg or any integer there inbetween. In one embodiment, the osmolarity of the liquid embryo development medium is about 82 mmol/kg.

Because of genotypic variation among different plant cell lines in response to liquid embryo development conditions it is necessary to optimize the liquid embryo development medium for each cell line. Some genotypes of pine produce fully developed embryos in medium totally devoid of non-permeating osmotic agents, whereas other genotypes may require exposure to low levels or exposure to these agents for limited time. One mode of our invention provides a method for using water soluble non-permeating osmotic agents at a low concentration or for limited time during a completely liquid embryo development phase. It is possible, using another mode of our invention, to gradually add or remove water soluble non-permeating osmotic agents at any time during the liquid embryo development, or prior to or after the liquid embryo development. This gradual change in non-permeating osmotic agents results in a gradual change in the osmotic conditions that the cells and developing embryos are exposed to, which more closely mimics the situation that occurs in vivo, where changes in the osmotic environment occur gradually overtime.

BRIEF DESCRIPTION OF THE DRAWINGS

FIG. 2. Growth, as measured by settled cell volume (SCV), of pine embryogenic tissues from cell line F in custom bioreactor during 5 growth cycles (a total time of 80 days). Growth, as measured by settled cell volume (SCV), of pine embryogenic tissues from cell line F in custom bioreactor during 5 growth cycles (a total time of 80 days). Solid bars are the total tissue production at the completion of each growth cycle. At the end of cycles 1 to 4, 1000 ml of tissue was retained to initiate the next cycle, and the remainder (shaded bars) was harvested.

DETAILED DESCRIPTION

Figure 1:
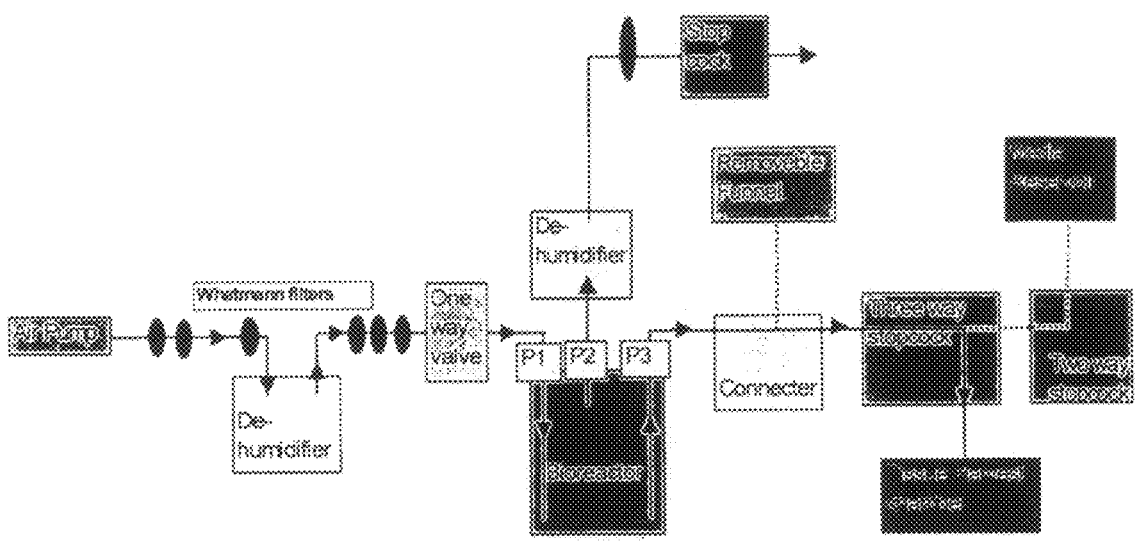
FIG. 1. Components and structure of bioreactor system.

Forestry and agricultural industries strive to create new and improved asexual methods for efficiently propagating trees with a desired trait. Somatic embryogenesis is an in vitro propagation technique for asexually creating somatic embryos that ultimately can be used for this purpose. Techniques that facilitate somatic embryogenesis, therefore, are highly desired.

As explained in detail below, the present invention provides new Liquid Embryo Development Media that (i) does not contain a non-permeating osmotic agent, or (ii) contains a low concentration of a non-permeating osmotic agent, or (iii) temporarily contains a non-permeating osmotic agent during plant cell incubation, e.g., during cell proliferation and/or embryo development, or (iv) contains a concentration of one or more media constituents that varies over time. Furthermore, the Liquid Embryo Development Media of the present invention do not require any solid surface for embryo development.

Hence, one of the inventive methods is an "all-liquid" embryo development strategy, which eliminates tedious, time-consuming physical manipulations of embryos associated with conventional strategies. This helps to increase the efficiency for producing embryos and germination-competent embryos, while reducing costs.

The "all-liquid" approach is readily scaled-up and, therefore, another aspect of the present invention is a bioreactor that produces large quantities of germination-competent embryos faster and more efficiently than is possible with existing techniques. Examples of suitable bioreactors include mechanical or gas-sparged mixing, bubble-column or airlift and temporary immersion, or ebb and flow. See Ziv M. Simple bioreactors for mass propagation of plants. In: Hvoslef-Eide A. K. and W. Preil (eds.) Liquid culture systems for in vitro plant propagation. Springer. Dordrecht, The Netherlands. Pages 79-93. 2005. Examples of commercially available bioreactors include the 30 liter GEA-Diessel Fermentation Bioreactor System by GEA liquid Processing, Columbia, Md. 21045, USA, and the 20/30 liter BioFlo 4500 Fermentor/Bioreactor System by New Brunswick Scientific, Edison, N.J. 08818, USA. Such bioreactors include those that are fully automated systems. Such systems may include means for manipulating various parameters such as, but not limited to, agitation speed, aeration rate, headspace pressure, temperature, pH, dissolved oxygen, nutrient medium additon, and sterilization.

Accordingly, the present methods for developing somatic embryos from proliferative plant cells can be performed in a single culturing vessel with minimal manual manipulations. This capability far exceeds what is possible with current commercial equipment and methods for producing germination-competent embryos.

To this end, methods for performing somatic embryogenesis can be generally summarized as including the following steps: (1) initiation, (2) embryogenic tissue proliferation, (3) morphological and physiological somatic embryo development, (4) embryo harvest and storage, and (5) embryo conversion into planting stocks.

The inventive methods and media of the present invention facilitate this procedure by markedly reducing the length of time it takes to produce germination-competent embryos and reduces the production cost of such embyros that are ready for embryo conversion into planting stock.

The embryo development step is particularly important because the quality of a somatic embryo is greatly influenced by culture and environmental conditions that proliferative cells are exposed to during this step. The quality of a somatic embryo is important because it is a characteristic that establishes whether or not an embryo can readily grow into a plant. The present invention provides a new liquid embryo development medium that facilitates and improves this process.

Factors that are known to influence embryo development include, but are not limited to (1) plant growth regulators, such as 2,4-D (2,4 dichlorophenoxyacetic acid), benzyladenine, and abscisic acid; (2) sugars, like maltose and sucrose, as sources of energy and as osmotic agents; (3) sources of nitrogen, such as amino acids like glutamine; (4) myo-inositol, (5) activated carbon, which both act as molecular "mops" or cleansing agents to absorb harmful chemicals that may accumulate during embryo development, and (6) inorganic salts and nutrients, are all factors that influence embryo development.

Non-Permeating Agents

In one aspect of the present invention, embryo development is performed in a Liquid Embryo Development Media that does not contain any non-permeating osmotic agent. In another aspect, the tissue may be temporarily exposed to a particular or a varying concentration of a non-permeating osmotic agent during the development stage.

Soluble substances or osmotic agents, which act as cellular osmotic agents, can be characterized by size according to whether they are readily taken up by cells due to osmosis. Small osmotic agents (e.g., sucrose, glucose, sugar alcohols, etc.) are readily taken up by cells and are referred to, as permeating or penetrating osmotic agents. Large osmotic agents that are generally believed to be excluded from the cytoplasm of plant cells are referred to as non-permeating or less readily permeating or penetrating.

Non-permeating osmotic agents, due to their large size, are believed to not readily pass through the pores of the plant cell wall. See Carpita et al., Science vol. 205, 1144-1147, 1979. When non-permeating osmotic agents are used as osmotic agents, the more negative osmotic potential of the external medium (due to the presence of these non-permeating osmotic agents) can only be counter-balanced by the cell in three ways: (1) uptake of other external permeating osmotic agents, (2) the synthesis of organic osmotic agents, or (3) water loss from the cells resulting in tissue dehydration.

An example of such a non-permeating osmotic agent is polyethylene glycol (PEG). PEG has frequently been used as a non-permeating osmotic agent, although it may have detrimental effects in addition to or separate from its intended osmotic effects. See Heyser and Nabors. Plant Physiol., vol 68, 1454-1459, 1981.

Conventionally, however, PEG is required for embryo development and it is generally thought that it is undesirable to exclude PEG from embryo development media. PEG is a water soluble polymer of general formula $H-(O-CH_2-CH_2)_n-OH$, where n is greater than or equal to 4. See The Merck Index—An encyclopedia of chemicals, drugs, and biologicals, $12^th$ Edition, 1996. It is common notation for each PEG to be followed by a number, which corresponds to the average molecular weight. For example, PEG 400 has average value of n between 8.2 and 9.1, and molecular weight range 380-420; whereas PEG 4000 has average value of n between 68 and 84, and molecular weight range 3000-3700, according to The Merck Index. The larger the size of the PEG, the less likely it can pass through a plant cell wall pore.

Thus, it is generally believed that certain high molecular weight compounds that do not freely traverse the cell membrane due to their large size can readily serve as non-permeating osmotic agents in vitro by imposing water stress. See Attree and Fowke, Plant Cell Tiss. Org. Cult., 35:1-35, 1993.

In this regard, larger molecules of PEG, such as PEG-4000 and PEG-8000 are frequently used as an osmotic agent during the embryo development phase of the conifer somatic embryogenesis process using gelled medium. Typically, PEG 4000 or PEG 8000 is used a constant level and at a relatively high concentrations.

In this regard, typically, PEG concentrations range from about 5 to 30%. These high concentrations of PEG result in increased embryo production. Even so, exposures to these high levels of PEG continuous during the embryo development phase of the regeneration process (typically lasting from 6 to 10 weeks) have been reported to have deleterious affects on embryo quality. Namely, PEG-treated embryos may have decreased germination and plant regeneration capacities.

Abscisic Acid (ABA)

ABA plays an important role in seed maturation and the suppression of precocious germination. In developing seeds, ABA stimulates accumulation of reserve substances and prepares embryos for dormancy. It also increases cold and desiccation tolerance of embryos. In maturing seeds of *P. glauca*, ABA content is the highest in megagametophytes preceding reserve deposition. Zygotic embryos develop in an environment with high ABA levels, and this hormone might be transported from megagametophytes to embryos.

Although the most common use of ABA is during the embryo development phase of conifer somatic embryogenesis, it has also been used effectively to improve both conifer embryogenic culture initiation and to improve re-growth of embryogenic cultures after retrieval from cryogenic storage. A concentration of 10 mg/l of ABA is not atypical. See, for instance, U.S. Pat. No. 5,677,185, which is incorporated herein by reference.

In somatic embryos of *Picea glauca*, abscisic acid stimulates embryo growth and inhibits precocious germination, i.e., it prevents embryos from developing too rapidly, which would otherwise cause them to develop immaturely. Hence, sometimes the absence of ABA causes abnormally fast-growing somatic embryos to develop, which are usually ungerminable because of inadequate preparation for germination. In somatic embryos of *P. glauca* x *P. engelmannii*, ABA enhances storage protein accumulation. Exogenous ABA is also capable of inducing the expression of genes coding some LEA proteins in somatic embryos of *Picea glauca* and *Pinus edulis*.

Nitrogen

According to the present invention, L-glutamine is a beneficial source of reduced nitrogen, which helps embryos develop. Another useful nitrogen source is casein, which is beneficial in initiation media, maintenance media, and liquid "bulk-up" media.

Vitamins

Vitamins also are useful in the context of tissue culture media. Vitamins and vitamin-like molecules such as thiamin (B1) nicotinic acid, pyridoxine (B6) and myo-inositol, for instance may be used in the inventive Liquid Embryo Development Media.

Sugars

The osmotic environment of developing embryos is important for both in vivo and in vitro embryo development (Stasolla and Yeung, Plant Cell Tiss. Org. Cult. 74:15-35, 2003). Low molecular weight carbohydrates that can be metabolized, such as sugars like sucrose, maltose and glucose, serve a nutritional role in morphogenesis in vitro since the cells and tissues are heterotrophic, which means they require an exogenous source of carbohydrates.

There also is evidence that such low molecular weight carbohydrates may play a regulatory or signaling role in morphogenesis and development of conifer somatic embryos. See Iraqi and Tremblay, J. Exp. Bot. 365:2301-2311. 2001. In addition, low molecular weight carbohydrates, like the sugars mentioned above and sugar alcohols, in cell and tissue culture media also influence the osmotic environment and are traditionally considered plasmolysing agents since they traverse both the cell wall and the cell membrane.

Accordingly, depending on the developmental stage and genotype of a particular embryogenic culture, the optimization of growth regulators levels, and imposition of osmoticum all can separately influence somatic embryo production and somatic embryo quality.

Embryo production for individual cell lines can vary depending on the particular Liquid Embryo Development strategy. Therefore, it is possible, and sometimes desirable, to appropriately optimize the Liquid Embryo Development Media for developing embryos from certain species and/or to increase the proportion of cell lines that produce embryos. For instance, any of the components described above or in Tables 1 and 2 for Liquid Embryo Development Media may be manipulated or assayed or titrated to determine the effects of a particular substance and its concentration on embryogenesis and successful embryo production.

Inorganic Nutrients and Salts

Embryo production and quality also is dependent on inorganic salts and nutrients. See, for instance, those nutrients and salts denoted in Table 2 below.

Formulations

With this in mind, the following exemplary Liquid Development Media can be applied according to the present invention. The present invention is not limited to these formulations, which may also comprise any of the facts described above, including specific inorganic nutrients and salts, such as those denoted in Table 2.

(a) No PEG Formulation

One formulation for the inventive Liquid Embryo Development Media of the present invention comprises (1) ABA, (2) myo-inositol, (3) maltose, (4) glutamine, and (5) activated carbon, but does not include the polyethylene glycol non-permeating osmotic agent. Neither does this Liquid Embryo Development Media contain gelrite or any other gelling agent.

(b) Low Concentration of PEG

Another formulation comprises (1) ABA, (2) myo-inositol, (3) maltose, (4) glutamine, (5) activated carbon, and (6) a low concentration of polyethylene glycol. A low concentration of PEG may be 0.5%, 1.0%, 1.5%, 2.0%, 2.5%, 3.0%, 3.5%, 4.0%, 4.5%, 5.0%, 5.5%, 6.0%, 6.5% or 7.0% or any integer in between.

(c) Temporary Exposure to PEG

Another Liquid Embryo Development Media comprises (1) ABA, (2) myo-inositol, (3) maltose, (4) glutamine, (5) activated carbon, and (6) contains , polyethylene glycol only for a short period of time. A short period of time may be 1 minute, 2 minutes, 5 minutes, 10 minutes, 20 minutes, 30 minutes, 45 minutes, 1 hour, 2 hours, 3 hours, 4 hours, 5 hours, 6 hours, 7 hours, 8 hours, 9 hours, 10 hours, 12 hours, 24 hours, 2 days, 3 days, 4 days, 5 days, 6 days, 7 days, 2 weeks, 3 weeks, 4 weeks, 5 weeks, 6 weeks, 7 weeks, or 8 weeks or more.

(d) PEG Modulation

Another Liquid Embryo Development Media comprises (1) ABA, (2) myo-inositol, (3) maltose, (4) glutamine, (5) activated carbon, and (6) contains varying concentrations of polyethylene glycol over the course of incubation.

Hence, one may increase or decrease the concentration of PEG over time by diluting, for example, a PEG-containing development solution with a Liquid Development Medium that does not contain PEG, or increase PEG concentration by doing the opposite replacement protocol.

Developing Germination-Competent Embryos

Suspension cultures are incubated in the dark at 25° C. on a shaker table and additional liquid suspension medium can be routinely added during the incubation period to maintain a desired cell density.

Cultures can be monitored weekly until they have grown to a mass or tissue density that is suitable for plating for embryo development. In this regard, the "settled cell volume" (SCV) is an indicator of liquid-suspended cell growth. It is well within the purview of the skilled person to determine a cell or tissue mass that is suitable for embryo development. For example, one may inoculate, in separate flasks or vessels, a different volume or amount of starting plant tissue or cells and then grow each culture to a particular density or SCV. The same aliquot from each of those flasks can then be taken at the same time point, or at numerous time points, and cultured in the Liquid Embryo Development Media of the present invention for a period of time to produce embryos. The number of embryos that are produced after the period of time can then be compared and related back to the amount of starting material and the respective culture densities. Thus, it is possible to say, after conducting such an assay, that "X" ml of proliferative cells, grown to "Y" SCV density, produces "Z" numbers of embryos for each experiment. Accordingly, one may establish the optimal values of starting material and cell density that produce a maximal, or otherwise desirable, number of embryos, which can then be conditioned for germination.

Embryogenic tissues that have been bulked up from either the traditional gel or the alternative liquid suspension media can be used as starting material to develop somatic embryos in the Liquid Embryo Development Media of the present invention.

Once such a desirable or optimal SCV density has been established, therefore, it is possible to eliminate optimization and proceed directly from a batch of starting material to embryo production. In this regard, it is well understood by those skilled in this field of art, that it is sometimes desirable to maintain a liquid culture of plant cells at that desired or optimal cell density or SCV. The person of skill in the art knows how to dilute cultures that exceed that desirable density or SCV. Likewise, if additional plant cells or tissue is needed, suspension cultures from single flasks can be used to establish additional flasks. Suitable media are described in Tables 1 and 2.

Conditioning

Hence, the all-liquid method of the present invention readily produces plant embryos, which then can be conditioned to produce germination-competent embryos. Germination-competent as used herein signifies embryos, when exposed to the appropriate environmental conditions, imbibe water, increase in size, become green (in light), elongate and develop a root. These growth and development changes of going from an embryo to a germinant are herein defined as germination and the resulting greening, elongated embryo with a root as a "germinant." Germinants, under appropriate environmental conditions, have continued growth and development with epicotyl (new shoot) growth emerging to result in plants. Thus, the transition from embryo to germinant is referred to as germination. In somatic or asexual embryogenesis, somatic cells may develop into plantlets following similar morphological steps as zygotes.

One particularly useful conditioning medium is 2M21. See Tables 1 and 2 for the composition of 2M21. Typically, conditioning medium is a gel encased within a vessel, such as a Petri dish. The present inventive method however also may employ a liquid-based version of the medium, whereby embryos are placed onto a filter paper that has been saturated with liquid medium. The embryos may be placed directly onto the saturated filter paper. Alternatively, the embryos can be placed onto a membrane, for instance, which is then placed onto the saturated filter paper, where the membrane is permeable in some respect to the liquid or to the moisture in the filter paper.

To prevent loss of moisture from the Petri dish-plated embryos, the dish may be sealed with any one of a number of tapes or wrappings. For instance, dishes may be sealed with Nescofilm™ when harvesting is done. These plates then can be stored for a desired period of time in the cold, i.e., at 4° C., although storage under these conditions is not always necessary. For instance, it may be desirable to bypass an entire cold storage step and proceed to germination. Directly proceeding to germination may require an embryo conditioning step, such as a high relative humidity conditioning step, which can have the added benefit of eliminating a cold storage incubation step. It is not necessary to "starve" the embryos during cold storage or at any other point in this process. By following such methodology, the embryos produced from the inventive Liquid Embryo Development Media may be matured to a germination-competent state.

EXAMPLE 1

Media

In the experiments described below, a number of different media are referred to by code. Tables 1 and 2, at the end of this Examples section, relate the components in each of these media and their associated codes. All media were adjusted to a pH of 5.8 prior to autoclave sterilization.

"Initiation" and "Maintenance" media can exist as gel or liquid forms and is made up of the following combination of media: WV5, DCR, and Mi3 (see Tables 1 and 2).

"Liquid Embryo Development Medium" ("Liquid EDM") is liquid MSG medium that either does not contain a non-permeating osmotic agent (e.g., polyethylene glycol) or gelrite (see Tables 1 and 2), contains a low concentration of a non-permeating osmotic agent, or contains a non-permeating osmotic agent for a limited time, or contains a non-permeating osmotic agent at varying concentration over the course of the embryo development phase.

"Conditioning," "Pre-germination," and "Germination" media is a combination of 2M21 and MODMS media (see Tables 1 and 2).

EXAMPLE 2

Determination of Settled Cell Volume

Cells and tissues grown in liquid medium can be grown in sidearm flasks for determining settled cell volume (SCV). The SCV of cells and tissues grown in sidearm flasks was determined whenever necessary using the following procedure:

Cells in liquid medium were swirled to ensure an even distribution of cells and liquid. The cell-liquid medium was tilted into the sidearm and left to settle for 30 minutes. After 30 minutes, a ruler was used to determine the height of settled cells in the total liquid. This height was then expressed as a percentage. For example, if the total height of the volume in the side arm was 100 mm and the amount of settled cells was at 50 mm, then this would equate to a settled cell volume of 50% SCV.

The SCV of cells grown in liquid medium in larger vessels, e.g., bioreactors, was similarly determined by stopping the rotation (agitation) propeller, allowing cells to settle for 30 minutes, and measuring, based on volume gradation marks on the vessel, the volume of settled cells and the total volume of liquid. For example, if the total volume of liquid and cells was 3 liters and the volume of cells was 2.0 liters this would equate to a settled cell volume of 66% SCV.

EXAMPLE 3

Development of Embryos in Liquid Medium Lacking Polyethylene Glycol

A test was done with suspension cultures from genotype A, testing the potential for embryo development in the three different media listed in Table 3.

Ten milliliters of suspension at 100% SCV per each genotype and flask was vacuum-aspirated and added to 30 ml of the respective treatment media (Table 3). The opening of each flask was closed with sterilized foam plug covered with aluminium foil. Flasks were agitated on a gyrotary shaker at 100 rpm in the dark growth room at 24° C. At end of weeks 1, 2 and 3 the SCV of the suspension cultures were determined as described in Example 2 and adjusted to an SCV of 50% if necessary. No dilution was done during weeks 4 and 5. After 5 weeks in the three different Liquid Embryo Development Media, fully developed cotyledonary embryos were only present in the suspensions grown on liquid embryo development medium (EDM) (treatment 3) that did not contain the non-permeating osmotic agent PEG.

EXAMPLE 4

Fully Developed Embryos on EDM Lacking Polyethylene Glycol from Several Different Genotypes Embryogenic suspension cultures of four loblolly pine genotypes A, F, G, and H were tested in this experiment using only liquid EDM (denoted as treatment 3 medium in Table 3). The same procedures were followed as in Example 3.

After 5 weeks fully developed cotyledonary embryos were obtained in 3 of the 4 genotypes; A and F, and G. This result showed that the present inventive findings were reproducible in two additional genotypes i.e., F and G, which had not been previously tested.

EXAMPLE 5

Viability and Germination-Competence of Somatic Embryos

The purpose of this experiment was to verify that the embryos produced in liquid EDM were viable and capable of germinating and growing into plants. Somatic embryos from liquid EDM obtained in Examples 3 and 4 were tested.

Embryos were harvested from the liquid EDM suspensions at week 5 by washing with sterile water the suspension on a membrane with pore openings (670 or 710 µm). The embryos were prepared for germination by exposure to a high relative humidity for 3 weeks at 24° C. This embryo conditioning method is described in U.S. patent application Ser. No. 11/413,105, which is incorporated herein by reference.

In this particular experiment, after the 3 week conditioning treatment, the embryos on the membrane were placed on modMS germination medium in a lighted culture room at 24° C. After 3 to 5 days the embryos were individually removed from the membrane and transferred directly to the surface of modMS germination medium and cultured for an additional 2 weeks in a lighted growth room at 24° C.

Embryo germination, which in this particular instance was estimated by identifying the emergence of a root from the embryo that was at least 1 cm long during this 2 week time period. Twenty-nine percent of the embryos harvested from liquid EDM germinated.

Germinated embryos were transferred to modMS medium in vessels for continued growth and development under in vitro conditions in lighted growth room at 24° C. Plants obtained from embryos developed in liquid EDM were transferred ex vitro to grow out in a greenhouse.

It is important to note that the combination of liquid EDM and high relative humidity conditioning drastically reduced the time required to produce germination-competent embryos. The embryos were harvested in liquid EDM after only 5 weeks and the embryos were conditioned for only 3 weeks. Hence, embryos were ready for germination after only 8 weeks.

This is much shorter period of time than is possible using standard conventional protocols. In those cases, embryos are developed on a standard gelled embryo development medium for typically 9 weeks. The subsequence cold, high relative humidity conditioning period is typically 7 weeks. Hence, germination-competent embryos only are available after approximately 16 weeks using conventional methods. Therefore, the inventive method employed here, namely a combination of embryo production in liquid EDM and a 3-week embryo conditioning period, results in germination-competent embryos in approximately half the time that is required using standard methods.

EXAMPLE 6

Production of Embryos in Liquid Embryo Development Media and the Germination of the Embryos from Additional Genotypes This experiment was performed to quantify embryo production, germination and conversion from somatic embryos produced in liquid EDM. Ten genotypes of loblolly pine were tested, namely: A, B, D, E, F, G, I, J, K and L The SCV of these 10 loblolly pine genotypes, which were maintained in liquid, was established at cell densities of 20% and 50%.

Treatment 1: place 6 ml of 100% SCV of cells dispensed in 30 ml of Liquid Embryo Development Media into Flask 1.

Treatment 2: place 15 ml of 100% SCV of cells in 30 ml of Liquid Embryo Development Media in Flask 2.

Excess fluid was removed from cells before culturing by transferring the cells onto a raft on a Buchner funnel and applying gentle vacuum aspiration. The initial SCV of the liquid cell suspension was measured before each flask was placed back on the gyrotary shaker in the dark growth chamber and monitored on a weekly basis for five weeks as described below.

Week 1: The SCV was measured as described in Example 2 and recorded. If the SCV of Treatment 1 was more than 20%, the culture was sub-cultured in order to maintain a tissue density of 20% during week 1. Treatment 2 was similarly sub-cultured, if the SCV was more than 50%.

Weeks 2 & 3: at week two and week three both Treatment 1 and Treatment 2 were maintained at 50% densities.

Week 4: cultures remained on the gyrotary shaker in the growth chamber and were not manipulated in any way this week.

Week 5: embryos were harvested from liquid in both flasks. An aliquot of 10 ml suspension culture was harvested from each flask that contained 30 ml total volume. The embryos were harvested from each flask as described in Example 6. The remaining 20 ml from each flask (treatment) was returned to gyrotary shaker for an additional four weeks.

After Week 5: the embryos harvested at the end of week 5 were conditioned and germinated as described in Example 6. Both Treatments 1 and 2 produced embryos that germinated using this process.

Treatment 2 produced embryos in 7 of the 10 genotypes and in 4 genotypes embryos germinated and were converted to plants. Treatment 1 produced embryos in 5 genotypes tested and 3 of these resulted in embryos that germinated and were converted to plants.

Maintaining the cultures at 50% total cells continuously (Treatment 2) resulted in good quality embryos, i.e., embryos that germinated, in four of the seven lines that produced embryos in culture.

The percentage germination ranged from 22% to 70% and that the percentage of conversion ranged from 6% to 41%.

EXAMPLE 7

Effect of Maltose on Embryos Developing in Liquid Culture

The purpose of this experiment was to investigate the role of maltose concentrations on somatic embryo production and embryo quality of embryos developed in liquid Embryo Development Media.

Suspension cultures of the following four loblolly pine genotypes, I, B, M, and N, were tested. Each cell line or genotype was initiated from an individual immature seed explant derived from a control pollinated cross of select parent trees of loblolly pine.

Five variations in the Liquid EDM listed in Table 1 were tested for development of loblolly pine somatic embryos in liquid. The five treatments were coded 1, 2, 3, 4 and 5 according to the concentration of maltose in the liquid medium, 0, 10, 20, 40 and 60 g/l, respectively.

Week 0: The proliferating embryogenic suspension cultures were poured in the side arm of the flask for 30 minutes to measure the settled cell volume (SCV) as described in example 2. A sub-sample of 12 ml of proliferating liquid suspension was removed for baseline development plating on five plates of MSG gelled embryo development medium for comparative purposes. The SCV measurement was recorded and the proliferating liquid suspensions were distributed among the treatments listed above.

Each treatment flask was initiated by placing 15 milliliters of 100% SCV onto a raft placed on a Buchner funnel and the excess liquid was removed through gentle vacuum aspiration. The tissues were then re-suspended into a 250 ml sidearm flask with 30 milliliters of Liquid Embryo Development Media with various maltose concentrations (from 0 to 60 g/l).

Once the cultures were re-suspended in liquid EDM the suspensions were poured in the sidearm to settle in the sidearm for thirty minutes to measure the SCV. Each treatment had three replicate flasks. The SCV measurements were recorded and the flasks were placed on the shaker in the dark, 24° C. growth chamber and monitored on a weekly basis for five weeks as described below.

Weeks 1, 2, & 3: the liquid embryo development suspensions were poured into the sidearm and allowed to settle in the sidearm for 30 minutes and the SCV measured and recorded. Each flask was sub-cultured as needed by adding liquid EDM to maintain the suspension density at 50%. This sequence of events was repeated at week two and week three.

Week 4: no media manipulation. The cultures were observed and placed back on the shaker.

Week 5: At week five the embryos were harvested as described in example 6 with the exception of using a 560 μm mesh to wash embryos. Half of the embryos were conditioned as described in example 6 and half were conditioned by the method described in U.S. Application Ser. No. 60/675, 949 simply for comparative purposes.

Fully developed embryos were produced in two cell lines, I and B in all liquid EDM treatments that contained maltose, but not in media lacking maltose (Table 5). Cell line M showed a positive response to increasing maltose by producing embryos that had not fully development on the highest (60 g/L) concentration of maltose. Cell line N did not respond to the maltose treatments in this experiment.

Increasing maltose concentration resulted in increased embryo production in cell line I. In this line, maltose at 60 g/l resulted in highest embryo production—on average 702 embryos per flask, from 2.4 grams starting tissue, or 290 embryos per gram starting tissue (Table 5).

Cell line B responded differently to increasing maltose concentration, with the highest embryo production of 526 embryos per flask on liquid EDM with 20 g/l maltose, from 2.4 grams starting tissue, or 218 embryos per gram starting tissue.

An important measure of efficiency and potential of an embryo development system for use in large-scale production is the number of embryos produced per total volume of medium used. This parameter provides a measure of embryo production cost. The following calculations show that our completely liquid embryo development invention demonstrates the potential to produce a very high number of embryos per total volume of medium used, and therefore has the potential to do so at a much lower cost compared to other systems in the prior art. A comparative calculation is provided below to show that our completely liquid embryo development system has embryo production levels per total volume of medium used exceeding similar values reported by another conifer embryo production bioreactor.

In these calculations the volume of medium discarded at each subculture was added to the final volume of medium. The average number of embryos produced (across maltose levels from 10 to 60 g/l) per ml of total media used was 8.3 per ml and 5.6 per ml for lines I and B, respectively.

The following explains how these values were calculated. For example, with line I in the 40 g/l maltose treatment, an average total of 70 ml of medium was used. That is, an average of 27 ml was discarded at the time of subculture and an average 43 ml of medium saved. Therefore, 70 ml was the average total volume of medium used to produce 526 embryos on average per flask Thus, the average number of embryos produced per total volume of medium used (both discarded and saved) was 526 embryos/70 ml, or 7.5 embryos per total ml media used.

This level of embryo production per total ml of medium in our liquid embryo development system exceeds levels reported by the bioreactor system of Attree. See U.S. Patent Application Publication 20026340594, where it is indicated that the volume of medium used to produce approximately 500 embryos required 450 ml of embryo development medium per week for 7 weeks. Therefore, approximately 3,150 ml of medium was used to produce 500 embryos. This is equivalent to 0.2 embryos per total ml of medium used. Furthermore, the Attree system is not a completely liquid embryo development system.

Using the above cited averages for embryo production from our completely liquid embryo development system (5.6 and 8.3 per total ml media used), our system represents an improvement of 28- to 42-fold improvement in embryo production per total ml of media used over the embryo production bioreactor system described by Attree (0.2 embryos per total ml of medium used).

The presently-disclosed liquid embryo development system also compares favorably with or exceeds embryo production per total ml of medium used in gelled embryo development systems (and is more amenable to scale-up and automation than gelled embryo production systems). For example, conventional embryo development plates that hold approximately 25 ml of gelled medium would have to produce on average 130 to 205 embryo per plate to be equivalent to our average embryo production from the completely liquid embryo development system. This assumes that only one plate of medium is used per each embryo harvest. If the tissue on the gelled embryo development medium is transferred to a new plate of medium during the embryo development process, and therefore 2 plates of gelled medium or 50 ml of gelled medium would be the required total volume of gelled embryo production medium. Therefore, such a gelled system would need to produce on average 260 to 410 embryos per plate to be equivalent to our average embryo production of 5.6 to 8.2 embryos per total ml of media used in the completely liquid embryo development example described herein. Such embryo production levels (i.e., exceeding 130 embryos per 25 ml of medium) are not achieved with most genotypes in gelled conifer embryo production systems.

Embryo yields may have been even higher, especially on the higher concentrations of maltose, if a smaller mesh size had been used to wash the embryos. The high standard deviations in column B, Table 5 data, on some maltose levels possibly reflect the loss of some embryos during the harvest wash.

EXAMPLE 8

Germination of Embryos from Example 7

Embryos were harvested and prepared for germination using two conditioning treatments: (1) exposure to high relative humidity for 3 weeks at 24° C. (Cond1), and (2) exposure to 4° C. for 3 weeks followed by high relative humidity for 3 weeks. Embryos were then germinated as previously described in Example 5.

Germination frequency of the embryos which developed in a completely liquid medium depended on both the genotype and the embryo conditioning treatment (Table 6). Genotype B embryos had the highest germination frequency, 41%, with embryo harvested from the 6% maltose liquid embryo development medium and subsequently conditioned for 3 weeks at high relative humidity (Cond1 treatment). Genotype I embryos had the highest germination frequency, 55%, with embryos harvested from the 2% maltose liquid embryo development medium and subsequently conditioned for 4 weeks in cold followed by 3 weeks high relative humidity (Cond2).

EXAMPLE 9

Development of a Custom-Made Bioreactor Capable of Bulking up Large Quantities of Embryogenic Tissues of Loblolly Pine Cost Effectively As mentioned above, the presently-disclosed all-liquid embryo development approach produces anywhere from about 5 to about 8 or more embryos per total ml of embryo development media. Hence, the all-liquid approach can be readily scaled up to produce large numbers of embryos per total volume of media. This approach is readily adaptable to a bioreactor system.

A bioreactor may be a vessel with a sealable lid or cover, which houses ports through which liquids and media can be delivered and withdrawn from the vessel. The vessel or its cover may be fitted with an inlet valve or port for delivering and extracting air or specific gases to and from the vessel. Each port or inlet or outlet may be fitted with appropriate filters to ensure sterility of the system and avoid contamination.

One such bioreactor model of the present invention is composed of a three to eight liter Pyrex three mouth spinner bottle labeled as "Bioreactor" in FIG. 1 whose custom made lid is fitted with three ports. The first port (P1) is used for supplying air to the bioreactor bottle. The air passes through a dehumidifying unit (Dehumidifier 1) and a system of six 0.2-micron filters before entering the bioreactor bottle. The dehumidifier units contain high-absorbent cotton. The second port (P2) provides ventilation, allowing the air to escape from the bottle. To ensure sterility, the exhaust is fitted with a dehumidifying unit (dehumidifier 2) and a 0.2-micron filter (as above). The third port (P3) is used for dispensing fresh liquid medium from the medium reservoir to the bioreactor bottle and also for harvesting tissues from the bioreactor bottle into the tissue harvest unit. Addition of media and harvesting tissues are performed by means of vacuum in the various units (bioreactor, Media reservoir and tissue harvest). These fully functional semi-automated bioreactors are employed for bulking up embryogenic tissues in the dark, 24° C. growth room. Capacity of these individual bioreactor units ranged from 3 to 8 liters. Another bioreactor unit was made to accommodate 36 liters.

When multiple bioreactors, each containing tissue from the same genotype or cell line, are run simultaneously the following components of the system can (but do not have to) be used in common: Air pump, media reservoir and tissue harvest chamber. If the multiple bioreactors each had different cell lines (genotypes), then different tissue harvest chambers are required for each line. The other components of the system (all other "boxes" and small black ovals (filters) in the FIG. 1) are control or filtration components and are required for each bioreactor unit. All components, except the air pump, are sterilized (autoclaved) prior to use.

(i) Materials for a Bioreactor

The following materials are useful for assembling and operating a bioreactor:

A three mouth stir bottle (e.g., Corning brand, available from Fisher Scientific, Product number 10-303F, available in capacities from 3 to 36 liters); A four-liter media bottle, Pyrex brand (available from VWR Scientific Products, product no. VWR-16157-250); Silicon tubing, ¼ inch ID×$\frac{7}{16}$ inch OD×$\frac{3}{32}$ inch wall thickness (VWR-62999-494); Whatman filters (for example, as available from VWR Sci., product no. VWR-28137-652); De-humidifiers (e.g., an autoclavable plastic bottle filled with cotton); Aquarium air pump; Sterile pipettes (25 and 50 ml); Pipette aid; Liquid culture medium (for example, Mi3 as in Table 1); Actively growing embryogenic tissue from either gelled medium or liquid suspension culture medium; Bunsen burner; Sterile gloves (VWR-PH2D7254); Stir plate; Magnetic stirrer bar; Parafilm or Nesco film.

(ii) Assembly and Inoculation of Tissue in Bioreactor for Bulk up of Cultures

In general, the inventive bioreactor arrangement may be assembled as depicted in FIG. 1. If desired, the unit may be wrapped with aluminum foil and sterilized using an autoclave, for instance, using a dry cycle of about 121° C. for 20 minutes. After unit has cooled to room temperature it may be placed in the sterile laminar flow-hood.

Under sterile conditions, embryogenic tissue may be placed into the bioreactor. Embryogenic tissue from gelled medium, for example, can be pre-prepared by weighing about 100 to 200 grams of fresh tissue into a sterile container prior to adding to bioreactor and adding Mi3 liquid media at the rate of 10 ml for every gram of tissue. Or, 100 to 200 ml of liquid suspensions at 100% SCV can be added to the bioreactor. Add necessary volume of Mi3-liquid media to the bioreactor bottle to maintain a desired tissue to media ratio, such as 1-gram tissue to 10 ml media.

Once the prepared tissue is placed in the unit, the bioreactor lid is closed and sealed with parafilm. The media reservoir to which the bioreactor is connected may be filled with a desired liquid medium, in the present case: about 4000 ml of Mi3 liquid. All tube connections are then sealed near the filters and dehumidifiers with parafilm.

If desired, the bioreactor can be placed on a magnetic stir plate to move an internal propeller for gentle agitation of the liquid suspension of tissue and/or embryos, such as at 50 rpm, with the air supply on, as previously described. The bioreactor arrangement as shown in FIG. 1 can be placed in dark at 24° C.

The growth of the tissues in the bioreactor is monitored by measuring the SCV at regular intervals, e.g., every 3 days, initially until the growth culture reaches approximately 100%

SCV, as well as convenient times, e.g., once a week, thereafter. Additional Mi3 liquid media may then be added during those monitoring periods to maintain a desired tissue to media ratio, such as of 1:2, as presently performed.

EXAMPLE 10

Bulk up of Embryogenic Tissues using the Custom Bioreactor for Large-Scale Embryo Production This example demonstrates the use of bioreactors for proliferation of embryogenic cultures of pine. Such cultures can be later utilized for liquid or gelled embryo development. There are advantages of using the bioreactors for both liquid tissue proliferation and the liquid embryo development phase. For example, it is possible to bulk-up large volumes of suspension cultures in bioreactors and by changing liquid medium within the same bioreactor vessel transition to the embryo development phase. This results in considerable savings due to reduced labor cost (i.e., greatly reduces handling tissue) and reduces chances for introducing contamination to cultures during production.

Significant improvements were made to the prototype custom bioreactor to make it contamination free, user friendly, and with the option for automation. This bioreactor design has the option for adding media and harvesting tissue without opening the bottle. This is also a much more predictable system and has the potential to produce large quantities of embryogenic tissue cost-effectively from many cell lines which is very vital for cost-effective production of millions of somatic embryo- derived plants.

A total volume of 9100 ml of cell line F embryogenic tissue was produced in this bioreactor over a period of 80 days and five growth cycles (Table 7). At the end of each growth cycle (except the last cycle 5), 1000 ml tissue was left in the bioreactor and the rest of the tissues were harvested. This 1000 ml of tissue served as the starting material for the next bioreactor cycle.

The average somatic embryo production from tissue samples obtained from each of the five growth cycles is shown in Table 7. Embryo production from tissue grown in the bioreactor during the $1^{st}$ and $2^{nd}$ growth cycles was equivalent or nearly equivalent to the baseline embryo production, which was 120 embryos/ml. The base line embryo production level was that obtained from tissue grown in a standard suspension flasks method, just prior to inoculating the bioreactor. Embryo production from tissue grown in the $3^{rd}$ and $4^{th}$ growth cycles declined by about one-third compared to the first cycle. Embryo production from tissue grown in the $5^{th}$ growth cycles declined by about two-thirds.

Based on the tissue and embryo production data from each of the growth cycles, it was possible to calculate the total potential number of somatic embryos that would have been produced if all of the tissues harvested from the five cycles of the bioreactor were plated for embryo development (Table 7). Accordingly, at the end of the $5^{th}$ cycle, the total potential embryo production was 1,181,600 somatic embryos if all cell line F tissues had been plated to embryo development medium.

The results also verified that it is possible to run bioreactors contamination-free for over 80 days.

EXAMPLE 11

Cost Effective Maintenance and Bulk up of Embryogenic Tissues

This example demonstrates cost effective maintenance and bulk up of embryogenic tissues from cell line I using the custom bioreactor and their potential use for large scale production of embryos. In addition, the embryo production capacity from tissue bulked up in the bioreactor is compared that from the same tissues bulked up in standard flasks.

The bioreactor was constructed and prepared for tissue inoculation as described in Example 9.

Tissue from the bioreactors was harvested at the end of a 10 to 14 day growth cycle (i.e., from the time of tissue inoculation to tissue harvest), when the SCV of the tissues in the bioreactor was at or near 100%. The tissues were plated for embryo development on MSG-based gelled embryo development medium (Table 1).

Tissues was also maintained in flasks and plated to development to serve as the "base line" control for the bioreactor.

Tissue from cell line I was maintained and bulked up continuously and contamination free over a period of 40 days. The tissues grew actively in the bioreactor throughout the culture period as evidenced by microscopic observations of the presence of healthy embryos in the cultures. A total volume of 5000 ml of embryogenic tissue was produced in this bioreactor over a period of 40 days and three growth cycles—1500 ml, 2000 ml and 1500 ml from the $1^{st}$, $2^{nd}$ and $3^{rd}$ cycles, respectively.

Tissue from each of the bioreactor growth cycles was plated on embryo development medium. Embryo production capacity of the tissue was similar in this cell line among each of the three growth cycles, with an average ranging from 52 to 65 embryos/ml of tissue. This exceeded the embryo production capacity of the base line control which produced an average of 34 embryos/ml of tissue. Using the tissue production data and the embryo production data, it was possible to assess the total embryo production potential of this cell line from tissue bulked up in the bioreactor. Base on the total potential amount of tissue produced by all the three growth cycles, a total potential production of 468,000 somatic embryos over a 40 day period of time would be obtained.

The results showed that the custom bioreactor can rapidly bulk up sufficient tissue for large-scale embryo production. The number of cycles per line, and therefore, the bulk up time required for large scale production depends on the cell line and the targeted production level. For example, with cell line F described in Example 10, where embryo production declined after 2 growth cycles it would be advantageous to have multiple bioreactors with each having fewer growth cycles. Whereas, some cell lines, for example as I described in this Example, where embryo production did not decline over 3 cycles, may require fewer bioreactors with more growth cycles per bioreactor. In either case, the results demonstrate the large-scale production potential of the custom bioreactors with minimal labor input during the tissue bulk up phase. In addition, this example showed that embryo production from tissue grown in the bioreactor was either equivalent to or higher than from tissue grown in a standard suspension in flask method.

EXAMPLE 12

Using a Bioreactor for Tissue Bulkup and Embryo Development

Maintenance and bulk up of tissue is achieved as described in Example 10 and 11. Mainetance media is then removed and replaced with Liquid Embryo Development Media. The SCV of the suspesion can be adjusted as described in Example 3, 6 and 7 and allowed to grow for approximately 5 weeks with any required dilutions as outlined in Examples 3, 6 and 7.

Germination capable embyos are removed from the bioreactor and germinated as previously described in Example 5. The person skilled in the art realizes and knows that any other bioreactor can be used to perform this experiment or any other experiment disclosed herein; see for instance the examples of various different bioreactors available to the skilled person as disclosed in the preceding text.

Tables

TABLE 1

Complete medium formulation. Refer to Table 2 for the inorganic salt and vitamin components.

| Component | WV5 INIT gel | DCR MAINT gel | DCR MAINT liquid | Mi3 BULK UP gel | Mi3 BULK UP liquid | EDM EMBRYO DEV. LIQUID | MSG EPROD gel | 2M21 COND gel | 2M21 COND liquid | modMS GERM gel |
|---|---|---|---|---|---|---|---|---|---|---|
| Inorganic salts & | See Table 2 | See Table 2 | See Table 2 | See Table 2 | See Table 2 | See Table 2 | See Table 2 | See Table 2 | See Table 2 | See Table 2 |
| Myo-inositol | 500 | 500 | 500 | 500 | 500 | 100 | 100 | 100 | 100 | 100 |
| Casein hydrolysate[a] | 500 | 500 | 500 | 500 | 500 | 0 | 0 | 0 | 0 | 0 |
| Sucrose | 0 | 15000 to 30000 | 30000 | 15000 to 30000 | 15000 to 30000 | 0 | 0 | 0 | 0 | 3000 |
| Maltose | 30000 | 0 | 0 | 0 | 0 | 2000 | 2000 | 2000 | 2000 | 0 |
| 2,4-D | 3 | 3 | 3 | 3 | 3 | 0 | 0 | 0 | 0 | 0 |
| BAP | 0.5 | 0.5 | 0.5 | 0.5 | 0.5 | 0 | 0 | 0 | 0 | 0 |
| ABA | 10 | 10 | 10 | 10 | 10 | 21 | 21 | 21 | 21 | 0 |
| Glutamine | 0 | 250 | 250 | 3000 | 3000 | 1450 | 1450 | 1450 | 1450 | 0 |
| Glycine | 0 | 2 | 2 | 2 | 2 | 0 | 0 | 0 | 0 | 0 |
| Phytagel[b] | 0 | 0 | 0 | 3000 | 0 | 0 | 0 | 0 | 0 | 0 |
| Gelrite[c] | 1500 | 2000 | 0 | 0 | 0 | 0 | 2000 | 2000 | | 2000 |
| Polyethylene glycol (PEG) | 0 | 0 | 0 | 0 | 0 | 0 | 70000 to 130000 | 0 | 0 | 0 |
| Activated carbon[d] | 0 | 0 | 500 | 500 | 500 | 1250 | 1250 | 0 | 0 | 5000 |

[a] Sigma C4523 casein hydrolysate
[b] Phytagel added in gelled Mi3 only.
[c] Gelrite (Gellan Gum, Schweizerhall, no. 89200, Merck, Kelco Div.
[d] Activated carbon (Nuchar SN, MeadWestvaco)

TABLE 2

Medium inorganic salt and vitamin formulation.

| Component | WV5 INIT | DCR MAINT | Mi3 BULKUP | MSG & EDM EPROD | 2M21 COND | modMS GERM |
|---|---|---|---|---|---|---|
| $NH_4NO_3$ | 700 | 400 | 200 | | | 800 |
| $KNO_3$ | 259 | 340 | 910 | 100 | 100 | 100 |
| KCL | 1327 | | | 745 | 745 | 745 |
| $CaCl_2 \cdot 2H_2O$ | | 85 | | 440 | 440 | 440 |
| $Ca(NO_3)_2 \cdot 4H_2O$ | 963 | 556 | 236 | | | |
| $MgSO_4 \cdot 7H_2O$ | 1850 | 370 | 247 | 370 | 370 | 370 |
| $Mg(NO_3)_2 \cdot 6H_2O$ | | | 257 | | | |
| $Mg(Cl)_2 \cdot 6H_2O$ | | | 102 | | | |
| $KH_2PO_4$ | 270 | 170 | 136 | 170 | 170 | 170 |
| $MnSO_4 \cdot H_2O$ | 15.16 | 22.3 | 10.5 | 16.9 | 16.9 | 16.9 |
| $ZnSO_4 \cdot 7H_2O$ | 8.6 | 8.6 | 14.7 | 8.6 | 8.6 | 8.6 |
| $CuSO_4 \cdot 5H_2O$ | 0.25 | 0.25 | 0.173 | 0.025 | 0.025 | 0.025 |
| KI | 0.83 | 0.83 | 4.16 | 0.83 | 0.83 | 0.83 |
| $CoCl_2 \cdot 6H_2O$ | 0.025 | 0.025 | 0.125 | 0.025 | 0.025 | 0.025 |
| $H_3BO_3$ | 31 | 6.2 | 15.5 | 6.2 | 6.2 | 6.2 |
| $Na_2MoO_4 \cdot 2H_2O$ | 0.25 | 0.25 | 0.125 | 0.25 | 0.25 | 0.25 |
| $NiCl_2 \cdot 6H_2O$ | | 0.025 | | | | |
| $FeSO_4 \cdot 7H_2O$ | 27.8 | 27.8 | 27.8 | 27.8 | 27.8 | 27.8 |
| $Na_2EDTA \cdot 2H_2O$ | 37.2 | 37.2 | 37.2 | 37.2 | 37.2 | 37.2 |
| Nicotinic acid | 0.5 | 0.5 | 0.5 | 0.5 | 0.5 | 0.5 |
| Pyridoxine HCL | 0.5 | 0.5 | 0.5 | 0.1 | 0.1 | 0.1 |
| Thiamine HCL | 1 | 1 | 1 | 0.1 | 0.1 | 0.1 |

TABLE 3

Three Liquid Embryo Development Media tested.

| Treatment no. | Liquid Embryo Development Medium with varying levels of polyethylene glycol |
|---|---|
| 1 | MSG with 7% polyethylene glycol (control) |
| 2 | MSG with 3.5% polyethylene glycol |
| 3 | MSG with 0 polyethylene glycol (EDM) |

TABLE 4

Effect of varying polyethylene glycol levels on development of loblolly pine somatic embryos in liquid medium for genotype A.

| Treatment no. | Liquid Embryo Development Medium with varying levels of polyethylene glycol | Degree of embryo development in liquid[a] |
|---|---|---|
| 1 | MSG with 7% polyethylene glycol (control) | 0 (none) |
| 2 | MSG with 3.5% polyethylene glycol | + |
| 3 | MSG with 0 polyethylene glycol (EDM) | ++ |

[a] 0 = only very early stage (precotyledonary) embryos observed
\+ = few larger, mid-stage (precotyledonary) embryos observed
++ = numerous, cotyledonary (fully developed) embryos observed

TABLE 5

Effect of maltose concentration on production of pine somatic embryos in liquid embryo development medium (EDM).

| Cell line | Maltose Level in liquid medium (g/l) | column A Fresh Wt. (g) starting tissue (per flask) | B Avg. ± st. dev. Embryos harvested (per 15 ml) | C Avg. Embryos (per ml) | D Total Avg. Potential Embryos (per flask) | E Avg. Embryos (per g tissue) |
|---|---|---|---|---|---|---|
| I | 0  | 2.6 | 0       | 0  | 0   | 0   |
|   | 10 | 2.3 | 232 ± 14 | 16 | 464 | 206 |
|   | 20 | 2.3 | 243 ± 60 | 14 | 486 | 216 |
|   | 40 | 2.2 | 263 ± 22 | 16 | 526 | 237 |
|   | 60 | 2.4 | 351 ± 66 | 20 | 702 | 290 |
| B | 0  | 2.8 | 0       | 0  | 0   | 0   |
|   | 10 | 2.5 | 232 ± 84 | 17 | 464 | 189 |
|   | 20 | 2.4 | 263 ± 76 | 18 | 526 | 218 |
|   | 40 | 2.6 | 211 ± 281 | 15 | 422 | 165 |
|   | 60 | 2.7 | 120 ± 20 | 8  | 240 | 89  | column A: Average fresh weight tissue to start each liquid embryo development flask
column B: Embryos harvested and counted from one-half the volume (15 ml) per flask
column C: Average number embryos per ml of liquid medium at harvest time (week 5)
column D: Total potential embryo yield per entire liquid volume (30 ml)
column E: Average number embryos per gram starting tissue (col. D/col. A)

TABLE 6

Effect of maltose concentration during liquid embryo development medium and subsequent embryo conditioning on germination frequency of pine somatic embryos.

| Genotype | Embryo Conditioning method | Germination (%) Maltose conc.[a] 1% | Maltose conc. 2% | Maltose conc. 4% | Maltose conc. 6% |
|---|---|---|---|---|---|
| B | Cond1: 3 wk HRH | 9 | 8 | 8 | 41 |
|   | Cond2: 4 wk cold & 3 wk HRH | 5 | 3 | 24 | 29 |
| I | Cond1: 3 wk HRH | 37 | 40 | 33 | 19 |
|   | Cond2: 4 wk cold & 3 wk HRH | 21 | 55 | 48 | 27 |

[a] The maltose concentration in the liquid embryo development medium.

TABLE 7

Tissue production from the bioreactor during 5 growth cycles of cell line F and subsequent average and potential embryo production.

| Bioreactor cycle | Tissue harvested (ml) | Embryos Produced (avg/ml) | Potential Embryo Production |
|---|---|---|---|
| 1 | 1600 | 120 | 307200 |
| 2 | 1500 | 107 | 256800 |
| 3 | 2000 | 78  | 249600 |
| 4 | 2000 | 78  | 249600 |
| 5 | 2000 | 37  | 118400 |
| total: | 9100 | — | 1181600 |

What is claimed is:

1. A method for developing plant embryos from proliferative plant cells, comprising
   (A) culturing proliferative plant cells for a first period of time in a liquid embryonic development medium that comprises
   (i) one or more phytohormones,
   (ii) a source of reduced nitrogen, and
   (iii) carbohydrate,
   wherein the liquid embryonic medium either (a) does not contain a non-permeating osmotic agent, or (b) comprises a low percentage concentration of a non-permeating osmotic agent selected from the group consisting of 0.5%, 1.0%, 1.5%, 2.0%, 2.5%, 3.0%, and 3.5%;

(B) separating the liquid embryonic medium from the embryos after expiration of the first period of time; and (C) conditioning the embryos by storing them in a high relative humidity environment for a second period of time prior to germination;

wherein the conditioned embryos are plant embryos developed from proliferative plant cells.

2. The method of claim 1, wherein the liquid embryonic development medium does not comprise a non-permeating osmotic agent.

3. The method of claim 2, wherein the non-permeating osmotic agent is polyethylene glycol.

4. The method of claim 1, wherein the phytohormone is abscisic acid (ABA) at a concentration from about 1 mg/L to about 100 mg/L.

5. The method of claim 4, wherein the concentration of ABA is about 21 mg/l.

6. The method of claim 1, wherein the source of reduced nitrogen is an amino acid.

7. The method of claim 6, wherein the amino acid is L-glutamine at a concentration from about 0.1 g/l to about 6.0 g/l.

8. The method of claim 1, wherein the carbohydrate is a sugar selected from the group consisting of maltose, sucrose, and fructose.

9. The method of claim 8, wherein the liquid embryonic development medium comprises from about 1% to about 10% maltose.

10. The method of claim 1, wherein the liquid embryonic development medium further comprises activated carbon.

11. The method of claim 10, wherein the concentration of activated carbon is from about 0.1 g/l to about 2.5 g/l.

12. The method of claim 10, wherein the concentration of activated carbon is about 1.25 g/l.

13. The method of claim 1, wherein the liquid embryonic development medium further comprises myo-inositol at a concentration from about 10 mg/l to about 1000 mg/l.

14. The method of claim 13, wherein the concentration of myo-inositol is about 100 mg/l.

15. The method of claim 1, wherein the liquid embryonic development medium does not contain a gelling agent.

16. The method of claim 1, wherein the osmolarity of the liquid embryonic development medium is from about 50 mmol/kg to about 200 mmol/kg.

17. The method of claim 1, wherein the osmolarity of the liquid embryo development medium is about 82 mmol/kg.

18. The method of claim 1, wherein the proliferative plant cells are incubated in the liquid embryo development medium for no more than 1 to 9 weeks during the first period of time.

19. The method of claim 1, wherein the proliferative plant cells are conifer cells.

20. The method of claim 19, wherein conifer is selected from the group consisting of Eastern white pine, Western white, Sugar pine, Red pine, Pitch pine, Jack pine, Longleaf pine, Shortleaf pine, Loblolly pine, Slash pine, Virginia pine, Ponderosa pine, Jeffrey pine, Pond pine, and Lodgepole pine, Radiata pine and hybrid crosses thereof.

21. The method of claim 1, wherein the embryos are stored in a high relative humidity environment for 1-7 weeks during the second period of time.

22. The method of claim 1, wherein step (C) is performed in a different vessel to that in which steps (A) and (B) are performed.

23. The method of claim 1, wherein the method steps are automated.

24. The method of claim 22, wherein steps (A) and (B) are performed in a bioreactor.

25. The method of claim 1, wherein the liquid embryonic development medium comprises 21 mg/L ABA, 1.25 g/L activated carbon, 100 mg/L myo-inositol, 1.45 g/l glutamine, and 2% maltose.

26. The method of claim 1, further comprising pre-preparing embryogenic tissue in a liquid medium containing more than 1.45 g/l glutamine prior to the culturing step of step (A).

27. The method of claim 26, wherein the liquid medium comprises 3 g/l of glutamine.

28. The method of claim 27, wherein the liquid medium is the Mi3 medium of Table 1 that contains no Phytagel.

29. The method of claim 28, wherein the pre-preparation of embryogenic tissue in the liquid medium prior to the culturing step of step (A) is performed in a bioreactor.

* * * * *